United States Patent [19]

McMickle et al.

[11] Patent Number: 4,641,860
[45] Date of Patent: Feb. 10, 1987

[54] COUPLING FOR FLEXIBLE TUBING

[75] Inventors: Robert L. McMickle; James T. Rumbaugh; Robert L. Netsch, all of Spirit Lake, Iowa

[73] Assignee: Berkley and Company, Inc., Spirit Lake, Iowa

[21] Appl. No.: 624,412

[22] Filed: Jun. 25, 1984

[51] Int. Cl.⁴ ............................................. F16L 35/00
[52] U.S. Cl. ..................................... 285/38; 285/150; 285/156; 285/242; 285/330; 285/398; 285/906; 285/923
[58] Field of Search ................. 128/334 C, 79, 132 R; 604/283, 905; 285/3, 38, 242, 260, 330, 371, 398, 150, 156, 906, 923

[56] References Cited

U.S. PATENT DOCUMENTS

| | | | |
|---|---|---|---|
| 102,443 | 4/1870 | Smith | 285/398 |
| 3,375,828 | 4/1968 | Sheridan | 604/119 |
| 3,853,122 | 12/1974 | Strauch et al. | 128/DIG. 20 |
| 3,863,622 | 2/1975 | Buuck | 128/DIG. 26 |
| 3,903,894 | 9/1975 | Rosen et al. | 128/DIG. 25 |
| 3,934,906 | 1/1976 | Shippey et al. | 285/371 |
| 3,954,102 | 5/1976 | Buuck | 128/DIG. 20 |
| 3,990,434 | 11/1976 | Free | 128/334 C |
| 3,992,045 | 11/1976 | Whittell, Jr. et al. | 285/371 |
| 4,009,711 | 3/1977 | Uson | 128/DIG. 20 |
| 4,201,202 | 5/1980 | Finney et al. | 128/79 |
| 4,235,227 | 11/1980 | Yamanaka | 128/79 |
| 4,318,396 | 3/1982 | Finney | 128/79 |
| 4,443,282 | 4/1984 | Stachitas | 285/235 |
| 4,537,183 | 8/1985 | Fogarty | 128/79 |
| 4,539,980 | 9/1985 | Chaney | 128/79 |

FOREIGN PATENT DOCUMENTS

| | | | |
|---|---|---|---|
| 162728 | 9/1905 | Fed. Rep. of Germany | 604/349 |
| 919620 | 10/1954 | Fed. Rep. of Germany | 285/398 |

*Primary Examiner*—Andrew V. Kundrat
*Assistant Examiner*—Anthony Knight
*Attorney, Agent, or Firm*—Faegre & Benson

[57] ABSTRACT

A coupling for fluidly connecting flexible tubing includes a rigid connector and an elastic retaining sleeve. The rigid connector has a main portion and a first and preferably second male end portions projecting therefrom with a fluid passage disposed within the male end portions and the main portion for fluid communication with the flexible tubing. The elastic sleeve member has a connector gripping section that circumferentially grips the main portion of the connector and a first and preferably second section for gripping the flexible tubing. The first and second sections are initially in a retracted position, folded-back over the connector gripping section and are movable to a second tubing-engaging position to grip the tubing. Preferably, handles are attached to the first and second gripping sections of the sleeve proximate their ends so that the sleeve may be gripped manually to facilitate movement of the first and second sections from the retracted position to the tubing-engaging position.

29 Claims, 11 Drawing Figures

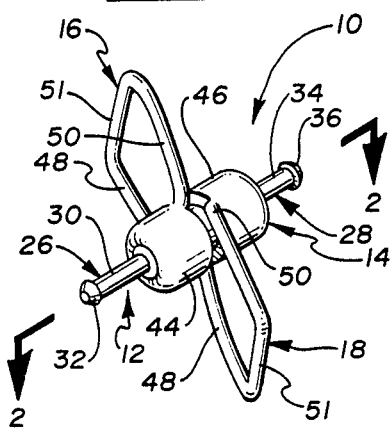
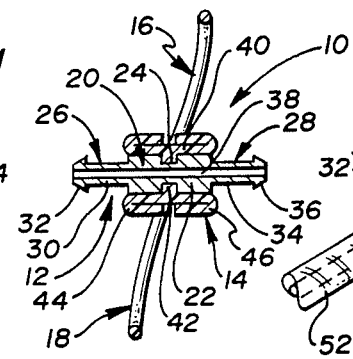
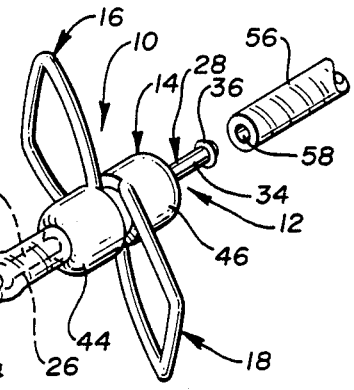
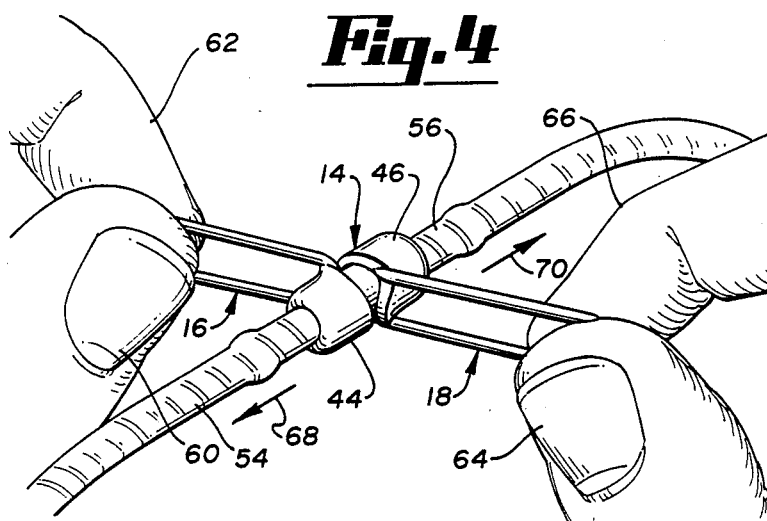
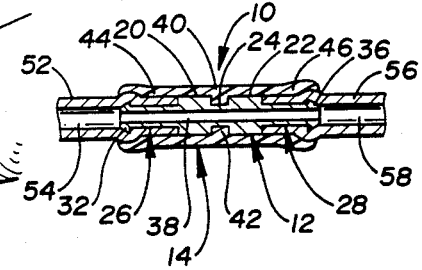
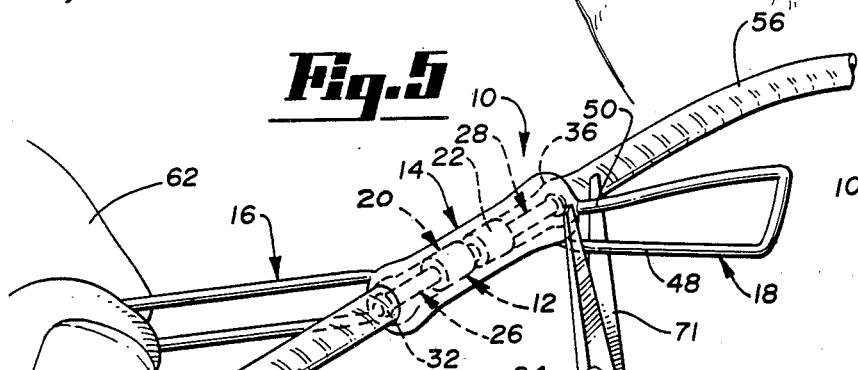
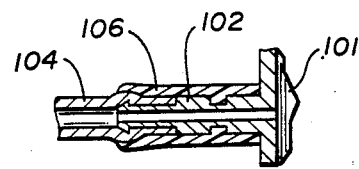
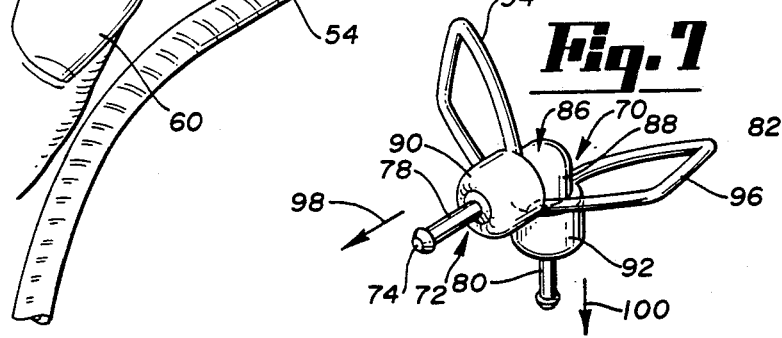
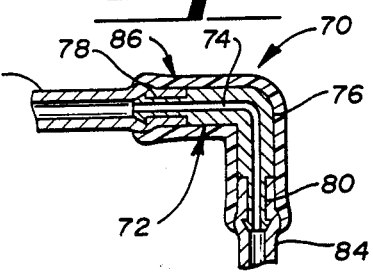

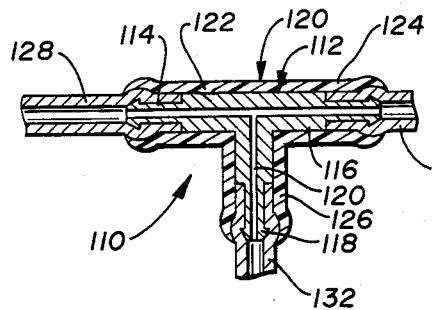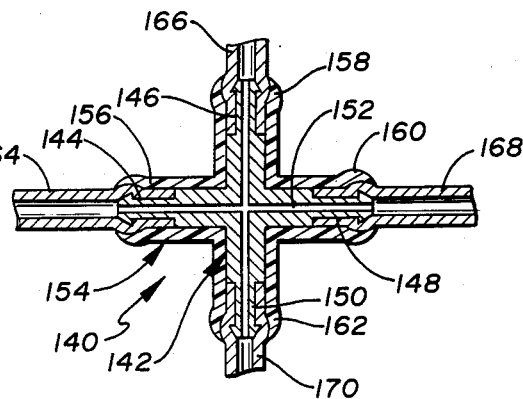

COUPLING FOR FLEXIBLE TUBING

BACKGROUND OF THE INVENTION

1. Field of the Invention

The present invention relates to couplings that fluidly connect flexible tubing; and in particular, the present invention relates to connectors that connect and securely hold tubing of implantable hydraulic devices.

2. Description of the Prior Art

Implantable devices that function or operate under hydraulic principles include flexible tubing sections for transporting fluid from one hydraulic element of the device to another. The tubing sections require connectors to connect and securely hold the tubing for many years after the device has been implanted. Some examples of hydraulic implantable devices include inflatable penile prostheses of the type disclosed in the Strauch et al U.S. Pat. No. 3,853,122, the Uson U.S. Pat. No. 4,009,711, the Finney et al U.S. Pat. No. 4,201,202, the Yamanaka U.S. Pat. No. 4,235,227, the Finney U.S. Pat. No. 4,318,396 and the Buuck U.S. Pat. No. 3,954,102, and urinary incontinence devices such as described in the Buuck U.S. Pat. No. 3,863,622 and the Rosen U.S. Pat. No. 3,903,894.

One specific example, namely the inflatable penile prosthesis, requires that fluid be transferred from a reservoir through tubing to the prosthetic member to inflate the prosthetic member so that an erection occurs. It is desirable that the several elements that comprise the inflatable penile prosthesis, such as the reservoir, pump and inflatable prosthetic members be implanted separately in different locations in the body. Typically, sections of elastic tubing are permanently attached to each of the hydraulic elements. The sections of tubing must then be attached to each other so that the various elements of the prosthesis are fluidly connected with each other.

The tubing is typically made of a medical grade elastomer that is highly elastic and highly compressive. The highly elastic and highly compressive characteristics have caused problems in connecting the tubing and retaining the tubing in a connected state. In many of the devices described above, the connectors used to connect the tubing have not securely held the tubing in place, causing hydraulic fluid to leak from the prosthesis and have required surgery to correct the leak.

One prior art method of connecting the tubing was to connect an end of each tubing section to a rigid stainless steel connector having a constant outer diameter. The tubing was pushed and expanded over the connector body with the fluid passages of the tubing communicating with the fluid passage of the connector. Ends of the tubing sections were slid over the connector and sutured to each other. This type of connection resulted in several problems. First, the tubing varies in wall diameter from batch to batch and the physician had to adjust the suturing techniques to the variations in the tubing wall thickness. Second, suturing of the tubing increased the time of implantation. Third, when the tubing was pressurized, there was a reduction in wall diameter at the suture site and reduced gripping by the tubing of the connector wall due to radial pressure exerted on the elastic tubing by the pressurized fluid. Leakage and an occasional failure resulted in some cases.

Other types of clamping devices that compressively clamp tubing against a rigid connector also have been found to be unsatisfactory for extended periods of time. Since the tubing is highly compressive, along with being high elastic, conventional clamps that hold the tubing by compressive forces, still permit the tubing to "creep" off the connector over an extended period of time.

SUMMARY OF THE INVENTION

The present invention includes a coupling for fluidly connecting flexible tubing. The coupling includes a rigid connector and an elastic sleeve. The rigid connector has a main portion and at least one male end portion extending therefrom with a fluid passage extending through the male end portion and the main portion for fluid communication with the flexible tubing. The elastic sleeve member has a connector gripping section and a tubing gripping section. The connector gripping section grips the main portion of the rigid connector. The tubing gripping section is positioned in an initial retracted position, folded-back over the connector gripping section and is movable to a tubing-engaging position for gripping the tubing when the tubing is connected to the male end portion of the connector. Preferably, a handle is preferably attached proximate to an end of the tubing gripping section of the sleeve. The handle facilitates manual gripping of the tubing gripping section for movement from the retracted position to the tubing-engaging position. The tubing gripping section, when in the tubing-engaging position, extends over the length of the portion of tubing connected with the male end portion, elastically gripping and securely holding the tubing.

BRIEF DESCRIPTION OF THE DRAWINGS

FIG. 1 is a perspective view of the present invention with the sleeve member in a retracted position.

FIG. 2 is a cross-sectional view of the connector taken along the line 2—2 in FIG. 1.

FIG. 3 is a perspective view illustrating connection of tubing sections to male end portions of the connector.

FIG. 4 is a perspective view illustrating manual gripping of the handles to move the connector sleeve from a retracted position to a tubing-engaging position.

FIG. 5 is a perspective view of the connector in a tubing-engaging position illustrating removal of one of the handles.

FIG. 6 is a cross-sectional view of the connector of the present invention in a tubing-engaging position with the handles removed.

FIG. 7 is a perspective view of an alternative embodiment of the present invention in the form of an elbow with the sleeve member in a retracted position.

FIG. 8 is a cross-sectional view of the alternative embodiment of FIG. 7 in the tubing-engaging position with the handles removed.

FIG. 9 is a cross-sectional view of an alternative embodiment of the present invention in the form of an outlet from an implantable device which shows the sleeve member in a tube-engaging position with the handles removed.

FIG. 10 is a cross-sectional view of another alternative embodiment in a T-configuration with the sleeve member in a tube-engaging position.

FIG. 11 is a cross-sectional view of yet another alternative embodiment of the present invention having a rigid connector with four male end portions for engaging four tubing sections with the sleeve member in a tubing-engaging position.

DETAILED DESCRIPTION OF THE PREFERRED EMBODIMENTS

The coupling device of the present invention is generally indicated at 10 in FIGS. 1 and 2. The coupling device includes a rigid connector 12, a sleeve member 14 and preferably a pair of handles 16 and 18 attached to the sleeve member.

The rigid connector 12 includes a primary cylindrical portion preferably having left and right annular raised shoulders 20 and 22. An annular groove 24 is disposed between the shoulders 20 and 22. Left and right male end portions 26 and 28, respectively, project outwardly from the main portion 20. The male portions 26 and 28 serve as nipples for insertably receiving end portions of tubing. The male portion 26 includes a longitudinal cylindrical section 30 and a frusto-conical end portion 32 disposed at a distal end of the cylindrical portion 30. Likewise, the male portion 28 includes a longitudinal cylindrical portion 34 and a frusto-conical end portion 36 disposed at a distal end of the cylindrical portion 34. The outer diameters of the cyindrical portions 30 and 34 are sufficiently large to permit an inner wall of the tubing to elastically engage the cylindrical portion. The frusto-conical end portions 32 and 36 each have a base diameter larger than the diameter of the cylindrical portions 30 and 34 which helps in part to prevent the tubing from sliding off the male end portions. The shoulders 20 and 22 are raised a distance from the outer surface of the cylindrical portions 30, 34, respectively, approximately equal to the wall thickness of the tubing when the tubing is engaging the male portions 26 and 28, respectively, to provide a substantially constant outer diameter along the length of the connector 12.

A fluid passage 38 is disposed longitudinally within the connector 12 extending from the left frusto-conical end portion 32 through the main portion 20 and to the right frusto-conical end portion 36. The passage 38 fluidly communicates with fluid passages of tubing sections when attached to the coupling device of the present invention.

The connector 12 is a rigid connector, preferably made of stainless steel or any other suitable medical grade metal. In addition, the connector 12 can be made of a medical grade plastic material, such as polysulfone which has sufficient rigidity for the male portions to accept tubing. One preferred polysulfone is sold under the trademark of UDEL by the Union Carbide Corporation of Connecticut. Preferably, the connector material includes a radio opaque substance, such as barium sulfate. The radio opaque substance provides a means after implantation for detecting, by fluoroscopic examination, whether the connector is connected.

The sleeve 14 is made of a suitable elastic medical grade material and has an inner connector gripping section 40 that elastically engages the main portion 20 of the connector 12. One suitable elastic medical grade material is a silicone resin marketed by Dow Corning of Michigan under the trademark of SILASTIC Q7-4750. Preferably, the sleeve 14 has an annular flange portion 42 that is disposed within the annular groove 24 of the connector 12 and serves to hold the sleeve 14 in position with respect to the longitudinal axis of the connector.

The sleeve 14 also includes left and right outer tubing grip sections 44 and 46, respectively. The outer sections 44 and 46 are initially folded back over the inner section 40 in a retracted position and are each sufficient long so that when the outer sections are moved to a tubing-engaging position, each outer section extends slightly past a bulge in the tubing formed due to the frusto-conical end portions 32, 36, respectively. The outer tubing sections 44 and 46 can be placed in the tubing-engaging positions by direct manual engagement or by a suitable gripping tool.

However, preferably handles 16 and 18 are used to place the outer tubing sections in the tubing-engaging position. The handles 16 and 18 are attached to the outer sections 44, 46, respectively, proximate their ends. Preferably, the handles 16 and 18 are of a generally U-shaped configuration having first and second leg portions 48 and 50 which are attached to the outer sections and a middle portion 51 connecting the leg portions 48 and 50, as illustrated in FIG. 1. The handles are sufficiently large so that they are gripped easily. The handles 16 and 18 are preferably molded with the sleeve as a unitary construction of the same medical grade elastomer. The material and configuration of the handles 16 and 18 permit easy severance of the handles from the sleeve after the tubing has been connected and secured to the coupling device of the present invention. Handle configurations other than the configurations described above are includable within the scope of the present invention.

The coupling device 10 provides an easy method for connecting flexible tubing of implantable devices during implantation. The method of connecting tubing sections using the coupling device 10 of the present invention is illustrated in FIGS. 3-5. As illustrated in FIG. 3, a tubing section 52 is connected to the male portion 26 of the connector 12 with the male portion 26 engaging the inner wall of the fluid passage 54 of the tubing 52. The frusto-conical end portion 32 pushes outwardly against the inner wall of the tubing and the tubing expands, resulting in a slight bulge. The tubing is pushed until its end abuts against the annular shoulder 20. Likewise, a tubing section 56 having a fluid passage 58 is connected to the male portion 28 in a similar fashion. The tubing sections 52 and 56 are generally fluidly connected to elements of an implantable device. The fluid passage of the connector 12 connects the fluid passages 54 and 58 so that the elements of the implantable device are fluidly connected.

After the tubing sections 54 and 56 are connected to the connector 12, the handles 16 and 18 are gripped, for example, with fingers 60 and 62, 64 and 66, respectively. The handle 16 is then pulled generally in a direction of arrow 68 along the longitudinal axis of the connector 12 and the handle 18 is pulled in the general direction of arrow 70 along the axis of the connector 12. Pulling the handles 16 and 18, as described above, moves the outer tubing gripping sections 44 and 46, in a direction of arrow 68 and 70, respectively, so that the outer sections 44 and 46 are moved from the retracted position over the respective tubing sections 54 and 56 to a tubing-engaging position, as illustrated in FIG. 5. As discussed previously, each outer section 44 and 46 is sufficiently long so that when placed in the tubing-engaging position, the outer sections 44 and 46 of the sleeve 14 extend past the bulge formed by the frusto-conical end portions 32 and 36. When in the tubing-engaging position, the sleeve 14 elastically grips the portions of the tubing 54 and 56 that are in engagement with the male portions 26 and 28 of the connector 12.

After the tubing 54 and 56 is connected by the coupling device 10 of the present invention, the handles 16 and 18 may be detached from the sleeve, for example, by simply cutting the handles with a scissors 71, detaching first the leg 48 and then the leg 50, as illustrated in FIG. 5.

As illustrated in FIG. 6, the coupling device 10 provides a compact structure that is ideally suited for implantable devices for holding highly elastic tubing securely for an extended period of time. The outer section 44 of the sleeve 14 elastically engages the portion of the tubing 54 in engagement with the male portion 26, extending past the frusto-conical end portion 32 and over the bulge of the tubing 54 caused by the frusto-conical end portion 32. Likewise, the section 46 of the sleeve 14 elastically engages the portion of the tubing 56 in engagement with the male portion 28 and extends past the frusto-conical end portion 36 over the bulge of the tubing 56 formed by the frusto-conical end portion 36. The outer sections 44 and 46 of the sleeve 14 tightly grip the tubing 54 and 56 so that forces caused by pressurized fluid moving through the tubing from one element of the prosthetic device to another are countered sufficiently so that the tubing 54 and 56 does not "creep" off the connector 12 over time. In one working embodiment, the tubing sections were held by the coupling device against an axial force in excess of 4 lbs. tensile strength. Typically, a tensile strength of at least 2 lbs. is considered necessary for implantable devices. In addition, the connector 12, sleeve 14 and tubing 54 and 56 provide a structural arrangement of a generally constant diameter that is only slightly greater than the outer diameter of the tubing.

In the preferred embodiment of the present invention, the addition of radiopaque material in the rigid connector aids in resolving whether a loss of hydraulic pressure is the result of the tubing working loose from the connector or is the result of some other problem, such as a pinhole developing in one of the hydraulic elements of the device. Although the coupling device of the present invention holds the tubing with greater than needed force, there may occur a situation wherein the tubing does work free. If the tubing does work free, the movement of the rigid connector out of its implanted position would be easily ascertainable using a fluoroscope.

An alternative embodiment 70 of the present invention is illustrated in FIGS. 7 and 8 having an elbow configuration. The embodiment 70 includes a connector 72 made of the same material as connector 12. The connector 72 has a fluid passage 74, a main portion 76 and first and second male portions 78 and 80, whose axes are disposed approximately 90° from each other, for engaging tubing sections 82 and 84. The main portion 76 has a larger outer diameter than the male portion 78 and 80, the difference being substantially equal to the wall thickness of the tubing sections 82 and 84 that are in engagement with the male sections 78 and 80.

A sleeve 86, shown in the retracted position in FIG. 7 and in the tubing-engaging position in FIG. 8, elastically grips the outer surface of the main portion 76 of the connector 72. The sleeve 86 has an inner connector grip section 88 and outer tubing grip sections 90 and 92 that are folded back in a retracted position over the inner section 88. Handles 94 and 96, similar to handles 16 and 18 described previously, are attached to the outer sections 90 and 92.

The tubing 82 and 84 is similarly connected by the connector 72 as described previously with reference to the connector 12. The handles 94 and 96 are then gripped and the outer sections 90 and 92 and are pulled in the general direction of arrows 98 and 100, respectively, so that the outer sections of the sleeve 86 are positioned over the tubing to engage the tubing as described previously.

It is also possible, as shown in FIG. 9, without departing from the invention hereof to provide an implantable device 101 with a projecting outlet connector 102 which can be coupled to tubing 104 using an outer sleeve 106 as shown in FIG. 9. The structure shown in FIG. 9 provides a superior coupling between an implantable device, such as a pump, and a tube used to move fluid from the pump to some other location within the body.

Another alternative embodiment having a T-configuration is illustrated in FIG. 10. The embodiment 110 includes a connector 112 having three male end portions 114, 116 and 118. The connector 112 also includes a fluid passage 120 fluidly communicating with the three male end portions 114, 116 and 118. A sleeve member 120 has three outer tubing grip sections 122, 124 and 126 that are initially folded back in a retracted position and are placed over tubing sections 128, 130 and 132, respectively, in a manner similar to the embodiment described in FIGS. 1–6. Suitable handles, preferably of the type illustrated in FIG. 1, are attached to the outer sections 122, 124 and 126.

Another alternative embodiment 140 is illustrated in FIG. 11. The embodiment 140 has a rigid connector 142 with four male end portions 144, 146, 148 and 150. A fluid passage 152 fluidly connects the four male end portions. A sleeve member 154 has outer sections 156, 158, 160 and 162 for elastically gripping tubing sections 164, 166, 168 and 170, all respectively, in a manner similar to the embodiment shown in FIGS. 1–6. Similarly, suitable handles, preferably like the handles illustrated in FIG. 1, are attached to the outer sections 156, 158, 160 and 162 of the sleeve member to facilitate moving the outer sections from a retracted to a tubing-engaging position.

Although the present invention has been described with reference to preferred embodiments, workers skilled in the art will recognize that changes may be made in form and detail without departing from the spirit and scope of the invention.

What is claimed is:

1. A coupling for fluid connection with flexible tubing, the coupling comprising:

a rigid connector with a fluid passage therethrough, the connector including a cylindrical main portion having a diameter substantially equal to the outside diameter of the flexible tubing and having a surface with at least one annular groove therein, and at least a first cylindrical male end portion having a diameter substantially equal to the inside diameter of the flexible tubing and having an enlarged diameter rigid distal end portion; and an elastic sleeve member having a main portion gripping section for elastically circumferentially gripping the main portion of the connector and including an interior gripping member insertable in the annular groove of the main section; and at least a first tubing gripping section positioned in a position overlapping the main portion gripping section and movable to an elastically engaged position over the tubing and the male end portion after the male end portion of the rigid connector is inserted into the tubing.

2. The coupling of claim 1 wherein the first tubing gripping section is sufficiently long to elastically grip substantially all of a portion of the tubing into which the first male end portion is inserted.

3. The coupling of claim 1 wherein the first male end portion includes a longitudinal section extending from the main portion and a frusto-conical end portion disposed on a free end of the longitudinal section having a diameter greater than the longitudinal section and the first gripping section having an end portion positionable past the frusto-conical end portion.

4. The coupling of claim 1 and further including:
handle means attached proximately to an end of the first tubing gripping section of the sleeve member for gripping to move the first tubing gripping section to the tubing-engaging position.

5. The coupling of claim 4 wherein the handle means includes a generally U-shaped member having first and second legs fixedly attached to the first tubing gripping section and a middle portion connecting the first and second legs.

6. The coupling of claim 5 and further including a second male end portion projecting from the main portion of the rigid connector with the fluid passage extending through the second male end portion and wherein the elastic sleeve includes a second tubing gripping section positioned in an initial retracted position over the connector gripping section and being movable to a second tubing-engaging position after the tubing is connected to the second male end portion of the connector.

7. The coupling of claim 6 wherein the handle means is also attached proximately to an end of the second tubing gripping section for gripping to move the second section to the tubing-engaging position.

8. The coupling ofo claim 7 wherein the main portion has an outside diameter greater than an outside diameter of the first and second male end portions.

9. The gripping of claim 6 wherein the second tubing gripping section is sufficiently long to elastically grip substantially all of a portion of the tubing into which the second male end portion is inserted.

10. The coupling of claim 6 wherein the second male end portion includes a longitudinal section extending from the main portion and a frusto-conical end portion disposed on a free end of the longitudinal section having a diameter greater than the longitudinal section.

11. The coupling of claim 6 wherein the second male end portion projects from the main portion on a side opposite from the first male end portion.

12. The coupling of claim 6 wherein the second male end portion projects from the main portion along an axis approximately 90° from an axis of the first male end portion.

13. The coupling of claim 7 wherein the handle means includes first and second generally U-shaped members each having first and second legs attached to the first and second tubing gripping sections, respectively, and a middle portion connecting the first and second legs.

14. The coupling of claim 1 wherein the rigid connector and the elastic sleeve cooperate to hold the tubing section with at least 4 lbs. tensile strength.

15. The coupling of claim 1 wherein the rigid connector is made of a radio opaque material.

16. The coupling of claim 1 wherein the rigid connector has a straight line fluid passage.

17. The coupling of claim 1 wherein the rigid connector has a fluid passage having a substantial bend therein.

18. The coupling of claim 1 wherein the main portion of the rigid connector is mounted on an implantable device and the fluid passage disposed within the rigid connector is operatively coupled to the interior of the implantable device.

19. The coupling of claim 1 wherein the rigid connector has second and third male end portions projecting therefrom and the fluid passage disposed within the second and third male end portions fluidly connecting the first, second and third male end portions and wherein the elastic sleeve member further includes a second and third tubing gripping section being positioned in an initially retracted position over the connector gripping section and being movable to a second tubing-engaging position after tubing sections are connected to the second and third male end portions, respectively, of the connector.

20. The coupling of claim 19 and further including:
handle means attached approximately to an end of the first, second and third tubing gripping sections of the sleeve member for gripping to move the first, second and third tubing gripping sections to the tubing-engaging position.

21. The coupling of claim 1 wherein the rigid connector includes second, third and fourth male end portions projecting therefrom and the fluid passage disposed within each of the male end portions for fluidly connecting the same and wherein the elastic sleeve member has second, third and fourth tubing gripping sections and the second, third and fourth tubing gripping sections being positioned in an initially retracted position over the connector gripping section and being movable to a second tubing-engaging position after tubing sections are connected to each of the male end portions of the connector, all respectively.

22. The coupling of claim 21 and further including handle means attached proximately to an end of each of the tubing gripping sections of the sleeve member for gripping to move each of the tubing gripping sections to the tubing-engaging position.

23. A method for fluidly connecting a first flexible tubing section with a second flexible tubing section to a rigid connector having a central portion and first and second male portions extending therefrom and an elastic sleeve attached to the central portion of the rigid connector with first and second tubing gripping sections wherein the first and second tubing gripping sections each include a handle for gripping, the method comprising:
attaching the first and second flexible tubing sections to the first and second male portions of the rigid connector; and
positioning the first and second tubing gripping sections of the sleeve over portions of the first and second tubing sections in engagement with the rigid connector so that the tubing is elastically held by the tubing gripping sections and wherein the first and second tubing gripping sections are positioned in the tubing-engaging position by gripping the handles and pulling on the handles in opposing directions until the first and second gripping sections are each in the tubing-engaging position.

24. An improved coupling having a rigid connector having at least one male end portion projecting therefrom and a main portion having a surface with at least one annular groove therein and having an enlarged distal end portion, the improvement comprising:

an elastic sleeve member having a connector gripper section and a tubing gripping section, the connector gripping section circumferentially gripping the main portion of the connector including an interior gripping member insertable in the annular groove of the rigid connector and the tubing gripping section being positioned in a position overlapping the connector gripping section and being movable to an elastically engaged position after the tubing is connected to the male end portion of the connector; and handle means attached approximately to an end of the first tubing gripping section of the sleeve for gripping to move the first tubing gripping section to the tubing-engaging position.

25. The improved coupling of claim 24 wherein the connector includes a second male end portion projecting from the main portion and wherein the elastic sleeve includes a second tubing gripping section positioned in an initial retracted position over the connector gripping section and being movable to a second tubing-engaging position after the tubing is connected to the second male end portion of the connector and wherein the handle means is also attached proximately to an end of the second tubing gripping section for gripping to move the second section to the tubing-engaging position.

26. The coupling of claim 24 wherein the main portion has an outside diameter greater than an outside diameter of the first and second male end portions.

27. The coupling of claim 24 wherein the second tubing gripping section is sufficiently long to elastically grip substantially all of a portion of the tubing attached to the second male end portion.

28. The coupling of claim 24 wherein the handle means includes first and second generally U-shaped members each having first and second legs attached to the first and second tubing gripping sections, respectively, and a middle portion connecting the first and second legs.

29. The coupling of claim 24 wherein the rigid connector is made of a radio opaque material.

* * * * *

UNITED STATES PATENT AND TRADEMARK OFFICE
CERTIFICATE OF CORRECTION

PATENT NO. : 4,641,860

DATED : February 10, 1987

INVENTOR(S) : Robert L. McMickle; James T. Rumbaugh; Robert L. Netsch

It is certified that error appears in the above-identified patent and that said Letters Patent are hereby corrected as shown below:

In claim 8, column 7, line 36, delete "ofo" and insert --of--.

In claim 9, column 7, line 39, delete "gripping" and insert --coupling--.

In claim 24, column 9, line 1, delete "gripper" and insert --gripping--.

Signed and Sealed this

Thirteenth Day of October, 1987

Attest:

DONALD J. QUIGG

Attesting Officer

Commissioner of Patents and Trademarks